United States Patent [19]

Singleton

[11] 4,196,353
[45] Apr. 1, 1980

[54] MICRORADIOGRAPHIC MICROSPHERE MANIPULATOR

[75] Inventor: Russell M. Singleton, Livermore, Calif.

[73] Assignee: The United States of America as represented by the United States Department of Energy, Washington, D.C.

[21] Appl. No.: 5,948

[22] Filed: Jan. 24, 1979

[51] Int. Cl.$^2$ .................... G01N 23/06; G01N 23/08
[52] U.S. Cl. .................................... 250/456; 250/451
[58] Field of Search ................... 250/451, 456, 439 R

[56] References Cited

U.S. PATENT DOCUMENTS 3,578,971  5/1971  Lasky .................................. 250/456

OTHER PUBLICATIONS

Henderson et al., "Microradiographic Characterization of Laser Fusion", *KMS Fusion Report No. KMSF* U543, Oct. 1976.

*Primary Examiner*—Alfred E. Smith
*Assistant Examiner*—T. N. Grigsby
*Attorney, Agent, or Firm*—R. V. Lupo; Roger S. Gaither; L. E. Carnahan

[57] ABSTRACT

A method and apparatus for radiographic characterization of small hollow spherical members (microspheres), constructed of either optically transparent or opaque materials. The apparatus involves a microsphere manipulator which holds a batch of microspheres between two parallel thin plastic films for contact microradiographic characterization or projection microradiography thereof. One plastic film is translated to relative to and parallel to the other to roll the microspheres through any desired angle to allow different views of the microspheres.

8 Claims, 2 Drawing Figures

MICRORADIOGRAPHIC MICROSPHERE MANIPULATOR

BACKGROUND OF THE INVENTION

The invention described herein was made at the Lawrence Livermore Laboratory in the course of, or under, Contract No. W-7405-ENG-48 between the United States Department of Energy and the University of California.

The invention relates to the examination of spherical members, and more particularly, to manipulation of microspheres for contact microradiographic characterization of projection microradiography thereof.

Spherical members, such as utilized in inertial confinement applications, require a high degree of symmetry, concentricity, and uniformity in surface finish. One of the significant problems associated with the production of such tiny spherical members (microspheres) is the precise manipulation of the microspheres for purposes of inspection and examination of concentric inner and outer surfaces, thickness, uniform surface finish, etc. For the characterization of the surface of thickness of microspheres (50 to 500 $\mu$m diameter) it requires a method of inspecting the entire surface area of the microsphere with fast, repeatable positioning thereof. Small vacuum chucks have been used for such manipulation, but such have drawbacks in aligning the required two axes of rotation. Also, apparatus have been developed for microsphere manipulation which involves using two flexible supportive, parallel members having flat surfaces, each attached to an end of a hollow capillary tube and holding a microsphere therebetween for examination. The latter approach is exemplified by copending U.S. patent application Ser. No. 906,815, filed May 17, 1978 in the name of Berthold W. Weinstein et al, and assigned to the assignee of this application. Other techniques have involved gluing down the microspheres for examination, but such prevents use thereof afterward, or using oil to hold the microspheres which results in contamination thereof. Another approach is obtaining on a film a radiographic image of the microspheres by irradiation of the microspheres with x-rays, such as described in a paper "Microradiographic Characterization of Laser Fusion" by T. M. Henderson et al, KMS Fusion Report No. KMSF U543, October 1976.

Optical interferometric techniques have also been utilized for examination of microspheres. However, such optical techniques are limited to use with optically transparent microspheres and thus not applicable for examination of optically opaque microspheres. Thus, there exists a need for a simple, yet effective, method for inspection of both transparent and opaque microspheres.

SUMMARY OF THE INVENTION

The present invention is directed to a method and apparatus wherein tiny hollow sphereical members (constructed) of either optically transparent or opaque materials, such as microspheres utilized in inertial confinement targets, are held and positioned by a manipulator for radiographic characterization to enable selection of spherical members of uniform wall thickness and proper surface finish. Basically, the microsphere manipulator utilizes two thin plastic films or layers which hold the microspheres therebetween, with at least one of the plastic films being connected to a control mechanism, such as a micrometer head, which moves the one plastic film with respect to the other such that the microspheres held therebetween are rotated under controlled conditions. The two plastic films are positioned adjacent a recording film or detector for high resolution, such that a contact or projection radiographic image of the microspheres is recorded on the recording film or detector when irradiated by x-rays from a source passing through the two thin films. The microspheres can be rolled so that they can be positioned and viewed at any desired angular orientation.

Therefore, it is an object of the invention to provide a method and apparatus for examination of hollow spherical members.

A further object of the invention is to provide a method and apparatus for contact microradiographic characterization of hollow spherical members.

Another object of the invention is to provide a microsphere manipulator which holds and rolls the microspheres between two parallel thin plastic films, movable with respect to one another, and located adjacent a recording film on which an image is imposed of the microspheres when irradiated by x-rays.

Another object of the invention is to provide a microsphere manipulator which holds and rolls the microspheres between two parallel thin plastic films, movable with respect to one another, and located adjacent an x-ray source, whereby an x-ray image of the microspheres is magnified onto an x-ray detector.

Other objects of the invention will become readily apparent from the following description and accompanying drawings.

DETAILED DESCRIPTION OF THE INVENTION

Figure 1:
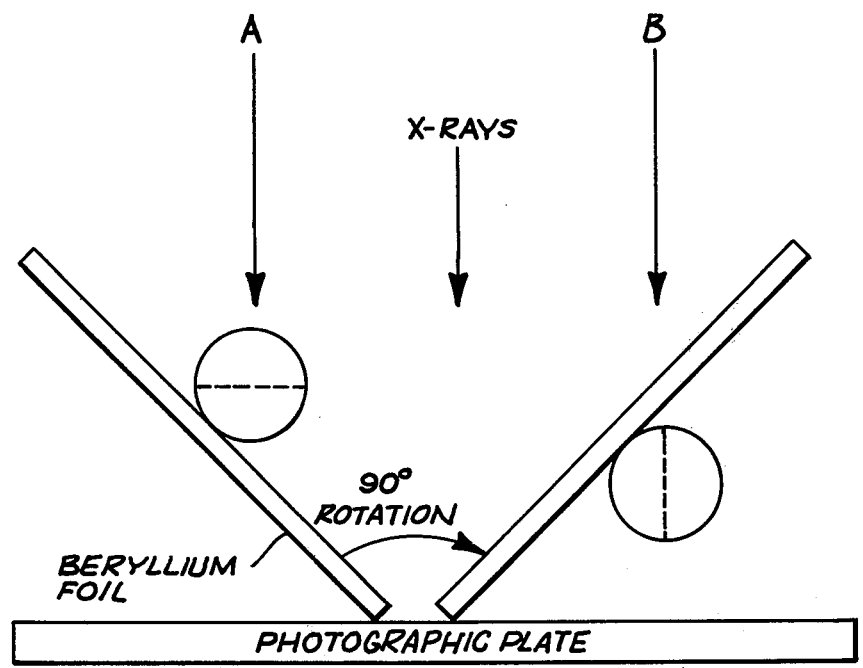
FIG. 1 schematically illustrates a prior art radiographic technique for examination of microspheres.

The invention involves a method and apparatus for examination of spherical members, constructed of either optically transparent or opaque materials, by contact microradiographic characterization or by projection microradiography. The spherical members may, for example, be hollow glass microspheres, having a diameter in the range of 50$\mu$ to 500$\mu$. The hollow glass microspheres may have an optically opaque coating on the outer surface thereof. Microradiography is a technique that can be used for characterization of optically opaque microspheres and also as an alternative to optical measurement of transparent microspheres. While the techniques using microradiographic characterization are known in the art, as indicated above with respect to the article by T. H. Henderson et al, the present invention provides for high resolution and permits examination of the microspheres at any selected position. The above-referenced Henderson et al microradiographic technique is illustrated in FIG. 1 which uses a beryllium wedge or foil on which the microsphere is held by oil, the wedge being rotated 90° as shown. Aside from the contamination problem mentioned above, resulting from the use of oil to hold the microspheres, the beryllium wedge approach allows for examination of only two views and the microsphere is held far from the photographic plate resulting in image resolution problems. By comparison, the present invention illustrated in FIG. 2 utilizes two parallel thin plastic films to hold and rotate the microspheres. One of the plastic films is in contact with a film or photographic plate or positioned adjacent an x-ray detector while the other is movable in at least two planes which provides for high image resolution and allows the microspheres to be rolled without slipping for examination of any portion thereof.

Figure 2:
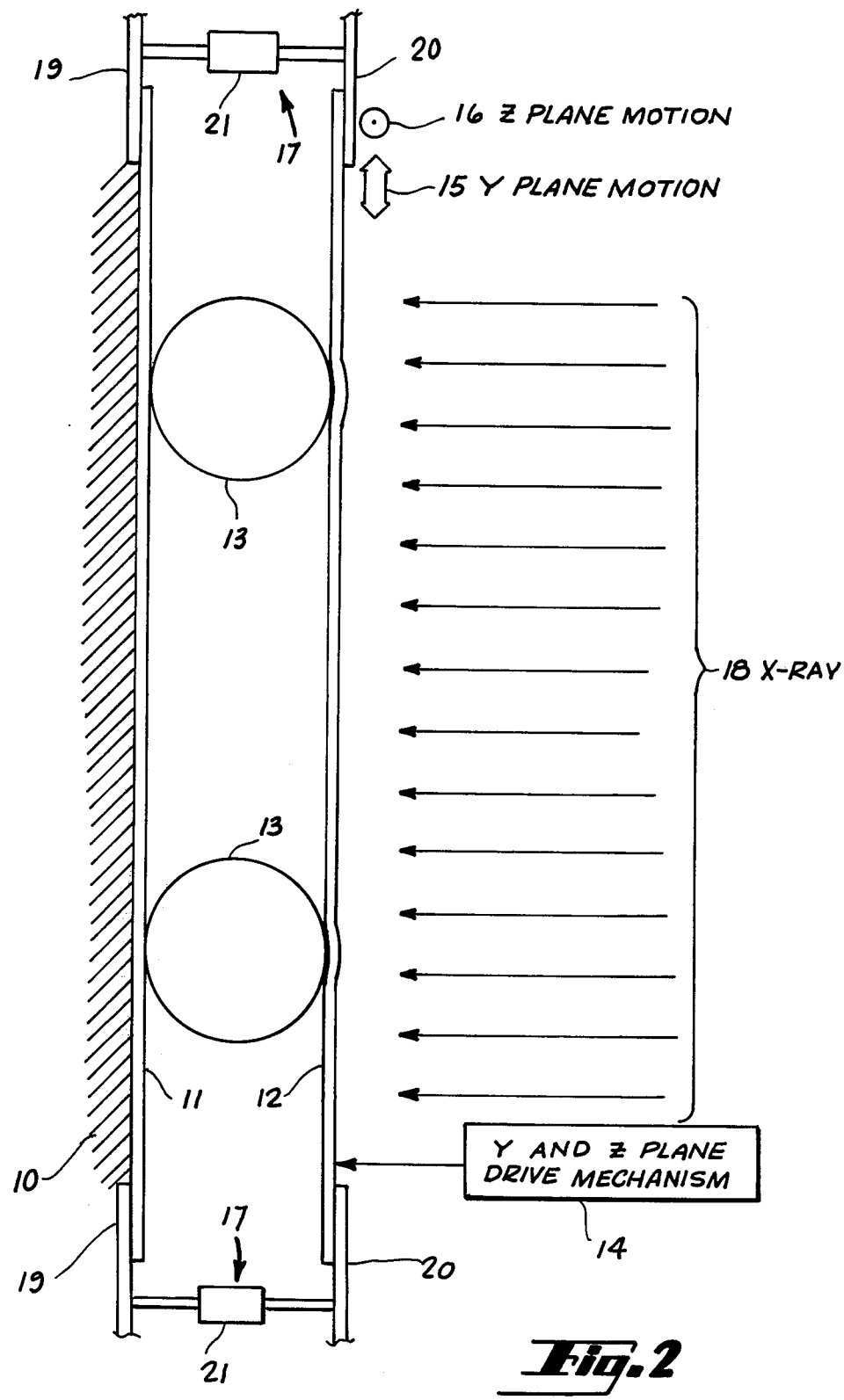
FIG. 2 schematically illustrates an embodiment of an apparatus made in accordance with the invention.

Referring now to FIG. 2, the apparatus basically comprises a film plate or record 10; a pair of parallel spaced members formed of plastic films or sheets 11 and 12 between which are positioned a batch of microspheres 13 (only two shown), the film 11 being placed against the emulsion side of film plate 10; a drive mechanism 14 connected to film 12 for moving same in Y and Z planes as indicated by arrows 15 and 16, respectively; a clamping mechanism generally indicated at 17 for adjusting the tension of the film 12 against the microspheres 13; and a beam of x-rays 18 from a source, not shown. Clamping mechanism 17 consists of a pair of film support members 19 and 20 movably positioned by an adjusting unit 21.

By way of example, the apparatus of FIG. 2 may be constructed as follows: the film plate 10 may be composed of Kodak HRP film. The plastic films 11 and 12 may be Formvar, made by Monsanto, which is transparent to x-rays and has a thickness of from 0.1 to 5 microns, with 2 microns being optimal for the energies described hereinafter. The x-rays 18 are produced by a source which may be of the bremsstralung type or of the monoenergetic type with peak energies ranging from 1 to 50 keV. The microspheres 13 may constitute hollow glass shells having a diameter of 50–500 microns, about 100 microns in this embodiment, and may contain a deuterium-tritium mixture and be coated with an opaque layer, if desired, for inertial confinement applications. For x-ray energies below 1 keV, thinner plastic films, down to 0.1 micron, may be desirable. Also, the plastic films 11 and 12 may be constructed of cellulose nitrate, but it has been found that Parylene is too fragile as a film material.

For example, the clamping mechanism 17 may be constructed such that support members 19 and 20 may constitute rings or sheeting having apertures therein through which x-rays 18 pass to irradiate the films 11 and 12 and microspheres 13 for recording on film plate 10. Support members 19 and 20 may be attached to respective plastic films 11 and 12 which are stretched taunt. The adjusting unit 21 constitutes wing nuts and bolts attached to support 20 as to allow movement of film 12 relative to film 11 in its Y and Z planes by drive mechanism 14, thereby permitting full two degree of freedom positioning and examination of the microspheres.

To carry out the method of this invention using the apparatus of FIG. 2, a batch of microspheres 13 to be inspected for symmetry, concentricity, and uniformity of surface finish are held in a fixed position between the two plastic films 11 and 12, the pressure or tension of the film 12 on the microspheres being controlled by clamping mechanism 17 so that the microspheres will roll without slipping when film 12 is moved in either a Y or Z plane by mechanism 14. The drive mechanism 14 may constitute micrometer heads, for example, such that the film 12 can be returnably moved parallel in either the Y or Z plane, as shown, to the film 11 and the emulsion side of film plate 10. Thus, the batch of mirospheres can be made to rotate simultaneously along an axis in either the Y or Z directions. The microspheres 13 are irradiated by x-rays 18 from the source. For example, using the apparatus having the parameters described above, the x-ray source yields a 0.2 micron spatial resolution at the edges of the microsphere image. The spatial resolution of the Kodak HRP film is rated better than 0.5 microns. The microradiographic images of the microspheres are examined and cataloged under a magnification of 200X, for example. Report UCRL-80148 by R. M. Singleton et al, presented at the Topical Meeting on Inertial Confinement Fusion, Feb. 7-9, 1978, San Diego, Calif. describes in greater detail the examination procedures for microspheres utilizing the method and apparatus of this invention and associated equipment specifically for microspheres proposed for inertial confinement applications.

While the apparatus for projection microradiography has not been illustrated, it merely involves the substitution of an x-ray detector for the photographic plate of the FIG. 2 apparatus, and positioning of the detector in spaced relation with respect to the parallel plastic films retaining the microspheres to be examined, such that an x-ray image of the mirospheres is projected or magnified onto the detector. The x-ray detector may be a film plate or a microchemical plate, as known in the art.

It has thus been shown that the present invention provides a method and apparatus for inspection of hollow spherical members by a contact microradiographic characterization or by projection microradiography which permits full two degree of freedom positioning. This is accomplished by simultaneously controllably rolling the hollow spherical members through any desired angle to allow different radiographic views to be taken of the spherical members, thereby advancing the state of the art, particularly for determining the symmetry, concentricity, and uniformity in surface finish of such hollow members.

While particular parameters and a particular embodiment of the apparatus for carrying out the examination method has been illustrated and/or described, modifications will become apparent to those skilled in the art, and it is intended to cover in the appended claims all such modifications as come within the spirit and scope of the invention.

What is claimed is:

1. An apparatus for contact microradiographic characterization of hollow spherical members comprising: a pair of spaced substantially parallel films of material transparent to x-rays for holding at least one associated spherical member therebetween, means for adjusting pressure of one of said pair of films against an associated spherical member, a film plate having an emulsion side positioned in contact with another of said pair of films, means for moving said one of said pair of films with respect to said another of said pair of films in Y and Z planes for rolling associated spherical members located therebetween, and means for directing x-rays through at least a portion of said films having associated spherical members therebetween for irradiating same, wereby microradiographic images of associated spherical members may be obtained.

2. The apparatus defined in claim 1, wherein x-rays have energies in the range of about 1-7 keV.

3. The apparatus defined in claim 1, wherein said pair of films have a thickness in the range of about 0.1-5 microns.

4. The apparatus of claim 3 wherein said films are constructed of plastic.

5. The apparatus of claim 3 wherein said films are constructed of cellulose nitrate.

6. A method for examining the symmetry, concentricity, and uniformity of the surface finish of hollow microspheres comprising the steps of: movable retaining at least one microsphere between a pair of parallel sheet-like members transparent to x-rays, positioning one of the members in contact with the emulsion side of a film plate, directing x-rays through the members so as to irradiate the hollow microspheres forming microradiographic images thereon on the film plate, and moving one of the parallel members in at least one direction causing rotation of the hollow microspheres 7. The method defined in claim 6, additionally including the step of adjusting the pressure of one of the members against the hollow microspheres to prevent slipping of same when rolled by the member.

8. A method for examining the symmetry, concentricity, and uniformity of the surface finish of hollow microspheres comprising the steps of: movably retaining at least one microsphere between a pair of parallel sheet-like members transparent to x-rays, positioning an x-ray detector adjacent one of the members, directing x-rays through the members so that an x-ray image of the microspheres is projected onto the x-ray detector, and moving one of the parallel members in at least one direction causing rotation of the hollow microspheres.

* * * * *